United States Patent [19]
Chu et al.

[11] Patent Number: 5,977,356
[45] Date of Patent: Nov. 2, 1999

[54] PROCESS FOR PREPARING CAPROLACTAM

[75] Inventors: Shiao-Jung Chu, Hsinchu; Hsi-Yen Hsu, Taipei; Ching-Tang Lin, Hsinchu; Kwang-Chic Lai; J. H. Tsai, both of Chang-Hua, all of Taiwan

[73] Assignees: Industrial Technology Research Institute, Hsinchu; Acelon Chemicals & Fiber Corporation, Chang-Hua, both of Taiwan

[21] Appl. No.: 08/887,174

[22] Filed: Jul. 2, 1997

[51] Int. Cl.$^6$ .................................................. C07D 201/08
[52] U.S. Cl. .............................................................. 540/538
[58] Field of Search ............................................... 540/538

[56] References Cited

U.S. PATENT DOCUMENTS

| | | | |
|---|---|---|---|
| 4,730,040 | 3/1988 | Vagt et al. | 540/538 |
| 4,730,041 | 3/1988 | Hutmacher et al. | 540/538 |
| 4,731,445 | 3/1988 | Hutmacher et al. | 540/538 |
| 4,963,672 | 10/1990 | Merger et al. | 540/538 |
| 5,717,089 | 2/1998 | Wolters et al. | 540/538 |

FOREIGN PATENT DOCUMENTS 729 944   9/1996   European Pat. Off. .

*Primary Examiner*—Mukund J. Shah
*Assistant Examiner*—Bruck Kifle
*Attorney, Agent, or Firm*—Sughrue, Mion, Zinn, Macpeak & Seas, PLLC

[57] ABSTRACT

A simple and single step process for producing caprolactam comprising reacting 5-formylvaleric acid or an ester thereof in a solvent of water and/or an alcohol with hydrogen and ammonia in the presence of a noble metal catalyst supported by a carrier at 80° to 300° C. under a pressure of 10 to 120 atm, whereby amination, acidification, dehydration and cyclization occur to obtain caprolactam.

17 Claims, No Drawings

PROCESS FOR PREPARING CAPROLACTAM

BACKGROUND OF THE INVENTION

1. Field of the Invention

The present invention relates to a process for preparing caprolactam. More particularly, the present invention relates to a process for producing caprolactam from 5-formylvaleric acid and its ester using water, an alcohol or a mixture as a solvent and using a noble metal catalyst supported by a Group II or IV oxide.

2. Description of the Prior Art

Caprolactam is an important raw material for nylon 6 and nylon 6 can be obtained from subjecting caprolactam to open ring polymerization. Nylon 6 has a great variety of uses, and it is mainly used for fibrous material and engineering plastics. As a fibrous material, nylon 6 can be made into clothes, carpets, tire cords and filter cloths. As an engineering plastic, nylon 6 can be made into component parts of automobiles, machines and electronic equipment.

Conventionally, caprolactam is prepared from cyclohexane oxime, as disclosed in U.S. Pat. Nos. 4,268,440 and 5,304,643. This process involves the Beckmann rearrangement of cyclohexanone oxime to obtain caprolactam. The disadvantages of this process are the cost of investment is too high and a great amount of undesirable ammonium sulfate waste is produced. Therefore, many other new processes have been established.

U.S. Pat. No. 4,730,040 uses methyl 5-formylvalerate as a starting material to produce caprolactam. In this process, methyl 5-formylvalerate is first hydrolyzed in the presence of an acidic catalyst at 30° to 200° C. to 5-formylvaleric acid, which is then reacted with excess ammonia and hydrogen in the presence of Raney nickel or Raney cobalt as a hydrogenation catalyst at 50° to 150° C. under superatmospheric pressure to form 6-aminocaproic acid. After the unreacted ammonia and hydrogen gas are removed, the aqueous mixture is heated to 150° to 370° C. under 100 bar to induce dehydrolyzation and cyclization of 6-aminocaproic acid to form caprolactam. Such process is very complicated and the yield is not high enough.

U.S. Pat. Nos. 4,730,041 and 4,731,445 use methyl 5-formylvalerate as a starting material and an alkanol as a solvent to produce caprolactam. First, methyl 5-formylvalerate is reacted with excess ammonia and hydrogen in the presence of an alkanol as a solvent and in the presence of a magnesium silicate-supported nickel catalyst at 40° to 130° C. under superatmospheric pressure to form methyl 6-aminocaproate. After the unreacted ammonia and hydrogen gas are removed, methyl 6-aminocaproate is converted into 6-aminocaproic acid and then formed to caprolactam by dehydrolyzation and cyclization or by direct de-alcoholization and cyclization. Although the process does not involve the hydrolyzation procedure of 5-formylvalerate, it suffers from the disadvantage that the starting material has a very low concentration (only 10%) and a great amount of alkanol should be separated and recycled.

Japanese Patent No. 29148 (1968) uses ammonia water as a solvent to convert 5-formylvalerate into caprolactam by direct cyclization in the presence of Raney nickel at 230° C. under 150 bar. This process suffers from the disadvantage that the yield is too low and fluctuates very greatly, and the pressure employed is too high, which can not meet the requirement for commercial production.

European Patent Application EP 729944 involves first contacting 5-formylvaleric acid with ammonia, contacting the resultant product with hydrogen in the presence of a hydrogenation catalyst to form 6-aminocaproate, and heating the resultant product at 200° to 350° C. for de-alcoholization and cyclization to produce caprolactam. Although such process employs lower pressure, an additional amination step is needed, thus making the process complicated.

U.S. Pat. No. 4,963,672 discloses another process for preparing caprolactam, wherein the 5-formylvaleric ester is reacted with excess ammonia and hydrogen gas in the presence of a ruthenium catalyst supported by alumina under 40 to 100 bar at from 80° to 140° C. for conversion into methyl 6-aminocaproate, the pressure is decreased to standard pressure, hydrogen is removed, and ammonia is replaced with xylene. After that, the pressure is increased to 70 to 100 bar and the resultant mixture is heated to 230° to 350° C. to convert methyl 6-aminocaproate into caprolactam by de-alcoholization and cyclization. This process is still complicated, and has the disadvantage that the pressure is increased, then decreased, and then increased again, and a great amount of xylene should be removed.

SUMMARY OF THE INVENTION

An object of the present invention is to solve the above-mentioned problems and to provide a process for preparing caprolactam. 5-formylvaleric acid and its ester can be converted into caprolactam via one single stage, in which amination, acidification, dehydration and cyclization is conducted in one single stage. The process of the present invention is much simpler, and complicated procedures, such as separation steps, and repeated procedures for increasing and decreasing the pressure can be eliminated.

To achieve the above-mentioned object, accordingly the present invention provides a process for producing caprolactam comprising:

(a) dissolving 5-formylvaleric acid or an ester thereof having the following structure in a solvent,

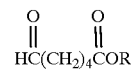

wherein R is a hydrogen atom, a $C_{1-8}$ alkyl group, an aromatic group or a cycloalkyl group, wherein the solvent is selected from the group consisting of water, an alcohol, and a mixture thereof; and (b) reacting the solution of 5-formylvaleric acid or an ester thereof with hydrogen and ammonia in the presence of a noble metal catalyst supported on a carrier at 80° to 300° C. under a pressure of 10–120 atm to undergo amination, acidification, dehydration and cyclization to obtain caprolactam.

DETAILED DESCRIPTION OF THE INVENTION

According to the present invention, the carrier-supported noble metal used as the catalyst has a high activity, and has double functions which make the starting material, 5-formylvaleric acid or its ester (or an ester thereof), react with excess hydrogen to undergo amination, acidification, dehydration and cyclization to obtain caprolactam in one single stage.

Suitable noble metals which can be used in the present invention are a Group VIIIB metal, such as platinum, palladium, ruthenium, and rhodium. The noble metal is present in an amount of 0.05 to 10.0 weight percent based on the total weight of the supported noble metal catalyst, preferably in the range of 0.1 to 10 weight percent, and most preferably in the range of 0.5 to 5 weight percent.

Suitable carriers for use in the present invention have an acid-base properties. Preferably the carrier is selected from the group consisting of an oxide of a Group II element, an oxide of a Group IV element, and mixtures thereof. The Group II element can be a Group IIA element or a Group IIB element, and the Group IV element can be a Group IVA element or a Group IVB element. Since the oxide of the Group II or Group IV metal can be formed into a carrier having characteristics of solid acid or solid base, it is particularly suitable for dehydration and cyclization of the intermediate 6-aminocaproic acid.

Representative examples of suitable metal oxides of metals of Group II and Group IV include silicon dioxide, zirconium dioxide, titanium dioxide, calcium oxide, magnesium oxide, and mixtures thereof.

To prepare the carrier-supported noble metal catalyst used in the present invention, the carrier should first be prepared. The salt or oxide of Group II or Group IV element (such as silicon, zirconium, titanium, calcium, and magnesium) was used for preparing the carrier by a conventional method, such as by coprecipitation, impregnation, surface coating, and ion exchange. Subsequently, the noble metal is applied on the carrier also by the above-mentioned conventional method. The source of the noble metal can be an oxide, nitrate, or chloride of the noble metal, or the noble metal powder itself.

Specifically, as demonstrated in the examples of the present invention below, the carrier of the present invention is immersed in a 5 to 50 wt % chloride salt solution of the noble metal for a long period of time, and then the impregnated carrier is filtered, evaporated and dried to obtain the carrier-supported noble metal catalyst. A suitable immersion time is at least 5 hours.

According to the present invention, the supported noble metal catalyst may be modified by a metal selected from the group consisting of zinc, tin, aluminum, tellurium, iridium, nickel, and mixtures thereof, so as to adjust the pH of the catalyst (to lower the acidity), increase the catalyst stability (life), increase the yield of caprolactam, and/or to decrease the formation of by-products. The modifying metal as mentioned above and the noble metal are simultaneously applied on the carrier by coprecipitation, impregnation, surface coating, and ion exchange or the modifying metal can be doped after loading the noble metal. The source of the modifying metal can be metal powders of zinc, tin, aluminum, tellurium, iridium, and nickel, or can be compounds of such modifying metal, such as an oxide, nitrate, and chloride thereof. One or more modifying metals also can be used.

Specifically, according to the example of the present invention below, the carrier of the present invention is immersed in a mixed solution containing a 5 to 20 wt % chloride salt solution of the modifying metal and a 5 to 50 wt % chloride salt solution of the noble metal for a long period of time, and then the impregnated carrier is filtered, evaporated and dried to obtain the carrier-supported noble metal catalyst.

Suitable immersion time is at least 5 hours. The amount of the modifying metal employed is 0 to 20 wt %, preferably in the range of 0 to 10 wt %.

The supported noble metal catalyst obtained (whether a modifying metal is present or not) should be calcined in an air stream at about 80° to 500° C. and formed into particles of a suitable size. Also, before use, the supported noble metal catalyst should be reduced with hydrogen at 180° to 300° C. for 4 to 24 hours in order to activate the catalyst.

The production of caprolactam according to the present invention, by the use of the specific supported noble metal catalyst, is described as follows. First, 5-formylvaleric acid or its ester (or an ester thereof) is dissolved in water, an alcohol, a mixed solution of water and an alcohol, or a mixed solution containing more than one alcohols. The solution of the 5-formylvaleric acid or its ester is then reacted with hydrogen and ammonia in the presence of the supported noble metal catalyst used in the present invention at 80° to 300° C. under a pressure of 10 to 120 atm to undergo amination, acidification, dehydration and cyclization to obtain caprolactam.

The 5-formylvaleric acid or an ester thereof suitable for use in the present invention has the following structure

wherein R is a hydrogen atom, a $C_{1-8}$ alkyl group, an aromatic group or a cycloalkyl group.

One aspect of the present invention is that the solvent used is water or an alcohol which is non-toxic, while in the conventional process for producing caprolactam, a toxic solvent such as an aromatic hydrocarbon is used. By using the non-toxic water or alcohol solvent of the present invention, the yield of caprolactam is higher, and caprolactam can still be obtained quickly even with a higher rate of the liquid feedstock.

When the solvent used is a mixture of water and an alcohol, and the catalyst used has double functions, that is hydrogenation and acid/base properties, once the intermediate 6-aminocaproate is formed, it is converted to 6-aminocaproic acid by hydrolyzation, which then quickly is converted to caprolactam by intramolecular dehydration and cyclization.

When the solvent used in the present invention is a mixture of water and an alcohol, the volume ratio of water to the alcohol is from 1:10 to 10:1, preferably in the range of from 3:7 to 7:3. The preferable alcohol is a linear or branched alcohol having from 1 to 6 carbon atoms such as methanol, ethanol, propanol, isopropanol, butanol, t-butanol, hexanol, and the like. The addition amount of the total solvent is preferably not higher than 85 wt %. When the solvent used is increased to higher than 85%, the yield of caprolactam will not be further improved. Preferably, the 5-formylvaleric acid or its ester is dissolved in the solvent in a concentration of 2 to 80 weight percent.

The reaction of the present invention can be conducted in a fixed bed reactor or a continuously stirred reactor. When conducted in a continuously stirred reactor, the supported catalyst is present in an amount of 5 to 40 wt % of the total amount of 5-formylvaleric acid (or its ester) and the solvent, preferably is present in an amount of 10 to 25 wt %. If the catalyst amount is too small, the residence time needs to be longer, while too much catalyst does not provide further improvement in the reaction. Preferably, the reaction residence time is 10 to 60 minutes, the reaction pressure is 10 to 120 atm, more preferably 30 to 90 atm. When the reaction pressure is higher than 120 atm, the yield of caprolactam is not effectively improved. The reaction temperature is between 80° C. and 300° C., preferably is in the range of 110° to 230° C. The molar ratio of ammonia to the 5-formylvaleric acid (or its ester) is 1 to 40:1, preferably 5 to 30:1. The molar ratio of hydrogen to the 5-formylvaleric acid (or its ester) is 1 to 20:1, preferably 3 to 15:1. When the reaction is completed, the product is separated by an internal sieve and ammonia and hydrogen are separated by pressure reduction. The unreacted ammonia and hydrogen obtained are advantageously recycled for reaction. The produced mixture containing caprolactam and the solvent is analyzed by gas chromatography to determine the yield of caprolactam.

When the reaction is conducted in a fixed bed reactor, the feeding rate of the liquid feedstock is preferably at 0.05 to 10 hr$^{-1}$, more preferably at 1 to 5 hr$^{-1}$. The other reaction conditions are the same as employed in a continuously stirred reactor.

Another important aspect of the present invention is that whether the starting material is 5-formylvaleric acid or a 5-formylvaleric acid ester, caprolactam can be obtained in a high yield via one single stage. In contrast, in the conventional process, a two stage or three stage reaction must be employed to obtain caprolactam, that is, 5-formylvaleric acid (or its ester) should be converted to 6-aminocaproic acid (or its ester), which is then cyclized to caprolactam by dehydration or de-alcoholization.

The following examples are intended to illustrate the process and the advantages of the present invention more fully without limiting its scope, since numerous modifications and variations will be apparent to those skilled in the art.

In the following examples, not only the process of the present invention is illustrated, other methods such as using a nickel catalyst or using other solvents are also demonstrated for comparison.

For the continuously stirred reaction, the reaction is conducted in two connected stainless autoclaves (300 mL). For the fixed bed reaction, the reaction is conducted in a stainless tubular reactor having a diameter of 0.5 inches. The catalyst is crushed and sifted to 40 to 80 mesh, and the catalyst amount used and the reaction conditions are as described in the following examples. After the reaction is completed, the unreacted ammonia and hydrogen should be removed by blowing a counter-current nitrogen, and the product is collected and analyzed by HP 5890 gas chromatography, in which an FID detector is used to detect the content of caprolactam. The conversion and yield shown in the examples are calculated as follows:

Conversion of 5–FVA or its ester (mole %) =

$$\frac{\text{moles of 5–FVA or its ester in the feedstock} - \text{moles of 5–FVA or its ester in the product}}{\text{moles of 5–FVA or its ester in the feedstock}} \times 100$$

Yield of caprolactam (mole %) =

$$\frac{\text{moles of caprolactam in the product}}{\text{moles of 5–FVA or its ester in the feedstock}} \times 100$$

Yield of 6–aminocaproic acid (mole %) =

$$\frac{\text{moles of 6-aminocaproic acid in the product}}{\text{moles of 5–FVA or its ester in the feedstock}} \times 100$$

5 – FVA = 5 – formylvaleric acid

Unless otherwise indicated herein, all parts, percents, ratios and the like are by weight.

EXAMPLE 1

46.84 g of zirconium butanoate [Zr(OC$_4$H$_9$)$_4$] and 183.09 g of tetraethylorthosilicate [Si(OC$_2$H$_5$)$_4$] were dissolved in 300 mL of ethanol. 10 wt % of ammonia water was added dropwise to the solution to adjust the basicity to a pH of about 10. A white precipitate was filtered off, washed, extruded as particles with a size of 0.2 cm×0.5 cm, and then calcined in an air stream at about 600° C. for 8 hours to obtain a catalyst carrier (65 g). The resulting crystals of the catalyst carrier were sifted to obtain particles of 40 to 80 mesh.

15 g of the above-obtained carrier particles were immersed in a ruthenium chloride solution (201 g, 200 mL) for 10 hours. The mixture was evaporated under reduced pressure and then dried at 105° C. for 16 hours. The dried carrier-supported catalyst particles were packed in a fixed bed reaction tube, and reduced with hydrogen at 220° C. for 6 hours. A mixed solution of ethyl 5-formylvalerate/water/ethanol (25:30:45 in volume ratio) was pumped through the reaction tube at a space velocity LHSV of 2.63 hr$^{-1}$. Simultaneously, hydrogen gas and liquid ammonia were fed into the reaction tube at rates of 60 mL/hr and 14 mL/hr, respectively. Hydrogen and ammonia were mixed in a mixing region and were contacted and reacted with the supported catalyst bed at 220° C. under 50 atm. The reacted mixture was then depressurized and brought to a stripper tube in which nitrogen gas was blown to remove the unreacted ammonia and hydrogen. The reaction product was collected and was analyzed by gas chromatography. The conversion of ethyl 5-formylvalerate was 100%, the yield of caprolactam was 85.3%, and the yield of 6-aminocaproic acid was 7.5%.

EXAMPLE 2

50 g of 0.5% rhenium modified 1% palladium/titanium dioxide supported catalyst (K-UCL-09, Nippon Engelhard, Japan) was crushed and sifted to obtain particles of 40–80 mesh. 15 g of the particles of the K-UCL-09 supported catalyst were packed in a fixed bed reaction tube. A mixed solution of methyl 5-formylvalerate/water/methanol (50:25:25 by volume ratio) was pumped through the reaction tube at a space velocity LHSV of 5.2 hr$^{-1}$. Simultaneously, hydrogen gas and liquid ammonia were fed into the reaction tube at rates of 480 mL/min and 56 mL/hr, respectively. Hydrogen and ammonia were mixed in a mixing region and were contacted and reacted with the supported catalyst bed at 130° C. under 70 atm. The reaction product was collected and was analyzed by gas chromatography. The conversion of methyl 5-formylvalerate was 100%, the yield of caprolactam was 78.5%, and the yield of 6-aminocaproic acid was 18.3%.

COMPARATIVE EXAMPLE 1

A NiO/WO$_3$ supported catalyst (T-4190, Nissan Girdler, Japan) was crushed and sifted to obtain particles of 40–80 mesh. 15 g of the particles of the T-4190 supported catalyst were packed in a fixed bed reaction tube and reduced with hydrogen at 300° C. for 8 hours. A mixed solution of ethyl 5-formylvalerate/water/ethanol (25:30:45 by volume ratio) was pumped through the reaction tube at a space velocity LHSV of 2.63 hr$^{-1}$. The other reaction conditions were the same as employed in Example 1. The results showed that the conversion of methyl 5-formylvalerate was 100%, the yield of caprolactam was only 8.8%, the yield of 6-aminocaproic acid was 58.5, and the yield of 6-aminocaproate was 21.2%. This indicates that if the catalyst used does not have high hydrogenation efficiency and acid-base properties at the same time, the yield of caprolactam is undesirably low.

COMPARATIVE EXAMPLE 2

15 g of alumina particles (40–80 mesh) was immersed in a ruthenium chloride solution (201 g, 200 mL) for 10 hours. The other procedures for preparing the supported catalyst were the same as employed in Example 1. The 2.5% ruthenium/alumina supported catalyst obtained was packed in a fixed bed reaction tube, and reduced with hydrogen at 220° C. for 6 hours.

A solution of methyl 5-formylvalerate (purity 98.7%) was pumped through the reaction tube at a space velocity LHSV of 5.2 hr$^{-1}$. The other reaction conditions were the same as employed in Example 2. The results showed that the conversion of methyl 5-formylvalerate was 98.5%, the yield of caprolactam was only 2.3%, and the yield of methyl 6-aminocaproate was 83.8%. This indicates that if the feedstock has does not include water or an alcohol, the intermediate methyl 6-aminocaproate is the most dominant product, which is hardly converted to caprolactam by direct de-alcoholization and cyclization.

EXAMPLE 3

5% rhodium/aluminum supported catalyst (33-75030, Nippon Engelhard, Japan) was crushed and sifted to obtain particles of 40–80 mesh. 15 g of the particles of the 33-75030 supported catalyst were packed in a fixed bed reaction tube and reduced with hydrogen at 300° C. for 8 hours. A mixed solution of ethyl 5-formylvalerate/water/ethanol (15:40:55 by volume ratio) was pumped through the reaction tube at a space velocity LHSV of 7.9 hr$^{-1}$. Simultaneously, hydrogen gas and liquid ammonia were fed into the reaction tube at rates of 54 mL/min and 50.5 mL/hr, respectively. Hydrogen and ammonia were mixed in a mixing region and were contacted and reacted with the supported catalyst bed at 250° C. under 30 atm. The other procedures not mentioned were the same as employed in Example 1. The results showed that the conversion of ethyl 5-formylvalerate was 100%, the yield of caprolactam was 90.3%, and the yield of 6-aminocaproic acid was 2.8%.

EXAMPLE 4

72.0 g of zirconyl chloride and 6.5 g of tin chloride were dissolved in 300 mL of distilled water.

10 wt % of ammonia water was added dropwise to the solution to adjust the basicity to a pH of about 10.

A white precipitate was filtered off, washed, extruded into particles with a size of 0.2 cm×0.5 cm, and then calcined in an air stream at about 600° C. for 8 hours to obtain a catalyst carrier. The resulting crystals of the catalyst carrier were sifted to obtain particles of 40–80 mesh.

15 g of the above-obtained carrier particles was immersed in a ruthenium chloride solution (201 g, 200 mL) for 24 hours. The mixture was evaporated under reduced pressure and then dried at 105° C. for 16 hours. The dried carrier-supported catalyst particles were packed in a fixed bed reaction tube, activated with hydrogen at 100° C. for 1 hours, then heated to 220° C. at a rate of 15° C./hr and activated with hydrogen at 220° C. for another 6 hours. A mixed solution of ethyl 5-formylvalerate/water/ethanol (80:5:15 by volume ratio) was pumped through the reaction tube at a space velocity LHSV of 5.3 hr$^{-1}$. Simultaneously, hydrogen gas and liquid ammonia were fed into the reaction tube at rates of 390 mL/min and 90 mL/hr, respectively. Hydrogen and ammonia were mixed in a mixing region and were contacted and reacted with the supported catalyst bed at 230° C. under 50 atm. The other procedures not mentioned were the same as employed in Example 1. The results showed that the conversion of ethyl 5-formylvalerate was 99.3%, the yield of caprolactam was 83.5%, and the yield of 6-aminocaproate was 1.7%.

EXAMPLE 5

The procedures for preparing the carrier and the supported catalyst were the same as employed in Example 1, except that the carrier particles were immersed in a mixed solution containing 201 g of ruthenium chloride and 0.12 g of iridium chloride. The supported catalyst was reduced by the same methods as described in Example 1. A mixed solution of isobutyl 5-formylvalerate/water/isobutanol (25:20:55 by volume ratio) was pumped through the reaction tube at a space velocity LHSV of 2.63 hr$^{-1}$. Simultaneously, hydrogen gas and liquid ammonia were fed into the reaction tube at rates of 120 mL/min and 28 mL/hr, respectively. Hydrogen and ammonia were mixed in a mixing region and were contacted and reacted with the supported catalyst bed at 180° C. under 30 atm. The results showed that the conversion of isobutyl 5-formylvalerate was 100%, the yield of caprolactam was 91.43%, and the yield of 6-aminocaproic acid was 3.8%.

EXAMPLE 6

The procedures for preparing the supported catalyst were the same as employed in Example 1, except that 15 g of the carrier particles used in Example 4 were immersed in a mixed solution containing 50 g of ruthenium chloride and 3.72 g of nickel nitrate. Subsequently, the catalyst was reduced with hydrogen, and the reaction of ethyl 5-formylvalerate was conducted, all by the same methods and the same conditions as employed in Example 1. The results showed that the yield of caprolactam was 90.3%, and the yield of 6-aminocaproic acid was 4.7%.

EXAMPLE 7

202.4 g of zirconyl chloride (ZrOCl$_2$.8H$_2$O) was dissolved in 1 L of distilled water, and then pH adjusted, filtered, washed, extruded, calcined and sifted by the same methods employed in Example 1 to obtain the carrier.

The procedures for preparing the supported catalyst were the same as employed in Example 1, except that the carrier was immersed in a mixed solution containing 0.51 g of platinum chloride and 0.16 g of tin chloride. The supported catalyst was reduced by the same method as employed in Example 1.

Subsequently, a mixed solution of ethyl 5-formylvalerate/water/ethanol (25:55:20 by volume ratio) was pumped through the reaction tube at a space velocity LHSV of 20 hr$^{-1}$. Simultaneously, hydrogen gas and liquid ammonia were fed into the reaction tube at rates of 260 mL/min and 40 mL/hr, respectively. Hydrogen and ammonia were mixed in a mixing region and were contacted and reacted with the supported catalyst bed at 230° C. under 90 atm. The results showed that the conversion of ethyl 5-formylvalerate was 97.8%, the yield of caprolactam was 80.7%, and the yield of 6-aminocaproic acid was 14.3%.

EXAMPLE 8

362 g of 40% silica gel (LUDOX AS grade) and 253 g of magnesium hydroxide powder were dissolved in 300 mL of ethanol, and then pH adjusted, filtered, washed, extruded, calcined and sifted by the same methods employed in Example 1 to obtain the carrier.

The procedures for preparing the supported catalyst were the same as employed in Example 1, except that the carrier was immersed in a solution containing 402 g of ruthenium chloride. Subsequently, the reaction was conducted by the same conditions employed in Example 1. The results showed that the conversion of ethyl 5-formylvalerate was 100%, the yield of caprolactam was 85.3%, and the yield of 6-aminocaproic acid was 7.6%.

EXAMPLE 9

The procedures for preparing the supported catalyst were the same as employed in Example 1, except that 15 g of the carrier used in Example 1 was immersed in a mixed solution containing 0.76 g of rhodium chloride and 0.12 g of iridium chloride. Subsequently, the reaction was conducted by the same conditions employed in Example 1. The results showed that the conversion of ethyl 5-formylvalerate was 100%, the yield of caprolactam was 88.1%, and the yield of 6-aminocaproic acid was 6.4%.

EXAMPLE 10

The procedures for preparing the supported catalyst were the same as employed in Example 1, except that 15 g of the carrier used in Example 1 was immersed in a solution containing 0.76 g of rhodium chloride. A mixed solution of ethyl 5-formylvalerate/water/ethanol (20:30:50 by volume ratio) was pumped through the reaction tube at a space velocity LHSV of 3.7 $hr^{-1}$. Simultaneously, hydrogen gas and liquid ammonia were fed into the reaction tube at rates of 370 mL/min and 46.5 mL/hr, respectively. Hydrogen and ammonia were mixed in a mixing region and were contacted and reacted with the supported catalyst bed at 230° C. under 50 atm. The results showed that the conversion of ethyl 5-formylvalerate was 100%, the yield of caprolactam was 90.5%, and the yield of 6-aminocaproic acid was 5.8%.

EXAMPLE 11

50 g of 5% platinum/alumina catalyst powder (13-70010, Nippon Engelhard, Japan) was placed in a stainless continuously stirred autoclave reactor. 150 mL of a mixed solution of ethyl 5-formylvalerate/water/ethanol (60:15:25 by volume ratio) was pumped through the autoclave reactor at a rate of 10 mL/min. Simultaneously, hydrogen gas with a pressure of 90 atm and liquid ammonia at a rate of 13 mL/min were fed into the reactor. The stirring rate was set to 300 rpm, and the reaction was conducted at about 180° C. The results showed that the conversion of ethyl 5-formylvalerate was 100%, the yield of caprolactam was 89.7%, and the yield of 6-aminocaproic acid was 7.7%.

COMPARATIVE EXAMPLE 3

The procedures employed in Example 11 were repeated, except that the catalyst used was 50 g of a Raney nickel (Grace Davison Raney 2724) and the feedstock was ethyl 5-formylvalerate with a purity of 98.7%. The results showed that the conversion of ethyl 5-formylvalerate was 93%, the yield of caprolactam was only 2.1%, and the yield of ethyl 6-aminocaproate was 78.6%.

While the invention has been described in detail and with reference to specific embodiments thereof, it will be apparent to one skilled in the art that various changes and modifications can be made therein without departing from the spirit and scope thereof.

What is claimed is:

1. A process for preparing caprolactam, comprising:
   (a) dissolving 5-formylvaleric acid or an ester thereof having the following formula

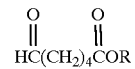

wherein R is a hydrogen atom, a $C_{1-8}$ alkyl group, an aromatic group or a cycloalkyl group, in a mixture of water and alcohol to form a solution; and
   (b) reacting the solution of the 5-formylvaleric acid or an ester thereof with hydrogen and ammonia in the presence of a noble metal catalyst supported by a carrier selected from the group consisting of an oxide of a Group II element, an oxide of a Group IV element, and a mixture thereof at 80° C. to 300° C. under a pressure of 10–120 atm, whereby amination, acidification, dehydration and cyclization occur to obtain caprolactam.

2. The process as claimed in claim 1, wherein the noble metal is selected from the group consisting of platinum, palladium, ruthenium, and rhodium.

3. The process as claimed in claim 1, wherein the Group II element is a Group IIA element.

4. The process as claimed in claim 1, wherein the Group II element is a Group IIB element.

5. The process as claimed in claim 1, wherein the Group IV element is a Group IVA element.

6. The process as claimed in claim 1, wherein the Group IV element is a Group IVB element.

7. The process as claimed in claim 1, wherein the carrier is selected from the group consisting of silicon dioxide, zirconium dioxide, titanium dioxide, calcium oxide, magnesium oxide, and mixtures thereof.

8. The process as claimed in claim 1, the noble metal of the supported noble metal catalyst is present in an amount of 0.05 to 10.0 weight percent.

9. The process as claimed in claim 1, wherein the supported noble metal catalyst is produced by coprecipitating, impregnating, surface coating, or ion exchanging the noble metal or its compound on the carrier,
   wherein the compound of the noble metal is selected from the group consisting of an oxide, a nitrate, and a chloride of the noble metal.

10. The process as claimed in claim 1, wherein the supported noble metal catalyst contains 0 to 20 weight percent of a modifying metal selected from the group consisting of zinc, tin, aluminum, tellurium, iridium, nickel, and a mixture thereof.

11. The process as claimed in claim 10, wherein the supported noble metal catalyst is produced by coprecipitating, impregnating, surface coating, or ion exchanging the noble metal or its compound and the modifying metal or its compound on the carrier,
   wherein the compound of the noble metal is selected from the group consisting of an oxide, a nitrate, and a chloride of the noble metal, and
   wherein the compound of the modifying metal is selected from the group consisting of an oxide, a nitrate, and a chloride of the modifying metal.

12. The process as claimed in claim 1, wherein the process comprises conducting step (b) in a fixed bed reactor or a continuously stirred reactor.

13. The process as claimed in claim 1, wherein the Volume ratio of water to the alcohol is from 1:10 to 10:1.

14. The process as claimed in claim 13, wherein the volume ratio of water to the alcohol is from 3:7 to 7:3.

15. The process as claimed in claim 1, wherein the 5-formylvaleric acid or its ester has a concentration of 2 to 80 weight percent in the solution.

16. The process as claimed in claim 1, wherein the molar ratio of ammonia to the 5-formylvaleric acid or its ester is from 5:1 to 30:1.

17. The process as claimed in claim 1, wherein the molar ratio of hydrogen to the 5-formylvaleric acid or its ester is from 3:1 to 15:1.

* * * * *